United States Patent [19]
Pauly et al.

[11] Patent Number: 6,146,857
[45] Date of Patent: Nov. 14, 2000

[54] METHOD FOR PRODUCING GLYCOGENS FOR USE IN COSMETICS BY CULTURING YEAST CELLS IN TWO PHASES

[75] Inventors: Gilles Pauly, Seichamps; Marc Pauly, Chateau-Salins; Jean-Marc Engasser, Ludres; Mohamed Ghoul, Nancy, all of France

[73] Assignee: Laboratoires Serobiologiques, Societe Anonyme, Pulnoy, France

[21] Appl. No.: 09/043,830

[22] PCT Filed: Dec. 13, 1996

[86] PCT No.: PCT/FR96/02008

§ 371 Date: Jun. 15, 1998

§ 102(e) Date: Jun. 15, 1998

[87] PCT Pub. No.: WO97/21828

PCT Pub. Date: Jun. 19, 1997

[30] Foreign Application Priority Data

Dec. 14, 1995 [FR] France ................................. 95 15310

[51] Int. Cl.[7] ............................. A61K 7/035; C12N 1/00; C12N 1/14; C12P 1/02; C12P 19/04
[52] U.S. Cl. ........................... 435/101; 424/69; 435/171; 435/255.1; 435/255.2; 435/255.21; 435/255.4; 435/255.7; 435/911; 435/921; 435/940
[58] Field of Search .................................. 424/78.03, 69; 435/41, 42, 101, 132, 169, 170, 171, 255.1, 255.2, 255.21, 255.4, 255.7, 911, 921, 940

[56] References Cited

U.S. PATENT DOCUMENTS

| | | | |
|---|---|---|---|
| 3,867,255 | 2/1975 | Newell et al. | 195/5 |
| 3,867,554 | 2/1975 | Sucher et al. | 426/60 |
| 3,888,839 | 6/1975 | Newell et al. | 260/112 R |
| 5,571,503 | 11/1996 | Mausner | 424/59 |

FOREIGN PATENT DOCUMENTS

| | | |
|---|---|---|
| 2 447 193 | 8/1980 | France . |
| 2 486 400 | 1/1982 | France . |
| 266 584 | 5/1989 | Germany . |
| 62 178 505 | 8/1987 | Japan . |
| 05 030 961 | 2/1993 | Japan . |

OTHER PUBLICATIONS (R)Dedhia et al., "Overproduction of glycogen in E. coli blocked in the acetate pathway improves cell growth . . . ", Biotechnol. Bioeng., 1994, vol. 44, issue 1, pp. 132–139.

(S) Peterson et al., "Enhancement of carbohydrates in a methylotrophic yeast . . . ", Enzyme Microb. Technol.; (1983) 5, 5, pp. 337–341.

*Primary Examiner*—David M. Naff
*Assistant Examiner*—Deborah K. Ware
*Attorney, Agent, or Firm*—Young & Thompson

[57] ABSTRACT

A process is provided for the production of glycogens or an extract rich in glycogens from yeast cells, and a cosmetic composition containing them. A given quantity of yeast cells, from a specific culture or recovered as residues of a fermentation process, is subjected to an operation of enrichment in intracellular glycogens by culturing in two phases in the presence of a carbon source. The metabolism of the yeast cells is then stopped. The membranes of the yeast cells are then at least partially disintegrated to free intracellular substances, and the freed intracellular substances are subjected to at least one precipitation to precipitate glycogens. A cosmetic composition comprising the glycogens is formulated in admixture with a dermatologically acceptable excipient.

16 Claims, No Drawings

METHOD FOR PRODUCING GLYCOGENS FOR USE IN COSMETICS BY CULTURING YEAST CELLS IN TWO PHASES

FIELD OF THE INVENTION

The present invention relates to the field of cosmetology, particularly the production of primary materials for cosmetics, and has for its object a process for the production of glycogens or extracts rich in glycogens from yeast cells, as well as the use of this glycogen or these extracts in cosmetic compositions and the resulting compositions.

BACKGROUND OF THE INVENTION

It is known that glycogen, a polysaccharide comprised of glucose and energetic reserve of living cells, is particularly abundant in yeast cells.

There are already known different processes for disintegration and treatment of yeast cells for the production of proteins, particularly recombinant ones, comprising the disintegration of said cells, the separation of the cellular debris, the recovery of the proteins and the purification of these latter.

Nevertheless, these known processes do not permit a preferential extraction of glycogens with high yield.

There are also known processes for the hydrolysis of yeast cells by thermal, enzymatic or chemical treatment, permitting producing yeast extracts for alimentary or therapeutic uses.

However, these known processes, often based on acid hydrolyses, lead to preparations in the form of hydrolysates containing together the proteins and the polysaccharides of yeast, and cannot supply yeast extracts specifically enriched in glycogens.

It is known moreover to extract glycogens from marine bacteria, and to subject these latter to a thermal and chemical treatment, to a trichloroacetic acid precipitation and to consecutive precipitations with ethanol.

These extractions, carried out on a laboratory scale, have only for their object to permit the analysis of the structure and the composition of the soluble glycogens and are not applicable other than to the specific type of cells in question, and are not applicable to cells having more resistant walls.

Finally, there already exist processes for the permeabilization of the cell walls of yeast and for the hydrolysis of the intracellular glycogens in glucose, so as to measure the amount present, these processes however cannot ensure extraction of the glycogen as such, particularly in an unhydrolyzed form.

OBJECT OF THE INVENTION

The problem addressed by the present invention consists accordingly in designing a process for the production of glycogens or extracts rich in glycogens from yeast cells, which can be easily practiced industrially for the production of glycogens in large quantity, having a high yield relative to the quantity of initial material treated, permitting extracting soluble and insoluble glycogens (connected to proteins of the cell walls) and hence to obtain extracts of variable glycogen content, particularly of very high values and in the non-hydrolyzed form, and adapted as the case may be to use residual yeasts from fermentation processes.

SUMMARY OF THE INVENTION

This problem is precisely solved by the production process according to the invention, characterized in that it consists essentially in taking a given quantity of yeast cells, supplied from a specific culture or recovered as residues of a fermentation process, subjecting said yeast cells to an operation of enrichment in intracellular glycogen in the presence of a carbon source, blocking the metabolism of said yeast cells, disintegrating at least partially the membranes of said yeast cells and subjecting the intracellular substances freed, to one or more overall or selective precipitations, as the case may be after the application of a fractionation, concentration, demineralization and/or decoloration operation.

DETAILED DESCRIPTION OF THE INVENTION

The above yeast cells can consist for example of yeasts recovered from different stages of existing processes for the production of yeast or for the use of yeast, for example in the course of producing beer.

However, said yeast cells can also be obtained by specific propagation processes carried out in fermenters containing a nutrient medium permitting the growth of yeast. The propagation of the yeasts can be carried out in a discontinuous manner, by adding all the elements of the nutrient medium at the beginning of culturing, or in a semicontinuous mode, by supplying the nutrient elements in the course of culture and during the latter, in a continuous or intermittent manner.

The yeasts used, such as brewery or bakery yeasts, having preferably a glycogen content, before enrichment, comprised between 1 and 40% (weight ratio of glycogen to dry cells), this initial content of glycogen determining particularly the duration of the enrichment phase.

According to a first characteristic of the invention, said operation of enrichment in glycogens can comprise a first revivification phase during which the yeast cells are disposed in a nutrient medium comprising particularly a carbon source, nitrogen and phosphorus, minerals and vitamins, and a second phase of maturation during which the yeast cells are disposed in a nutrient medium containing at least one carbon source, preferably a sugar such as glucose or saccharose, at a concentration comprised between 1 and 700 g per liter of nutrient medium, a source of nitrogen, preferably ammoniacle and/or various mineral elements.

During this enrichment operation, the yeast cells disposed on or in a nutrient medium transform the carbon source present in said medium into intracellular glycogens, under aerobic or anaerobic conditions.

The revivification and maturation phases can be carried out in a discontinuous manner, by adding all the elements of the nutrient medium adapted to the phase in question at the beginning of each of said culture phases, or in a semicontinuous manner, by supplying the nutrient elements in the course of said culture phases and throughout these latter, in a continuous or intermittent manner.

The maturation phase is preferably conducted under conditions of limitation as to nitrogen source, thermal shock or excess mineral salts. Its duration can vary from several minutes to about 20 hours as a function of the desired intracellular glycogen content (generally from 10 to 40% by weight relative to the mass of dry yeast cells).

According to another characteristic of the invention, the blockage of the metabolism of the yeast cells, for the deactivation of the enzymatic and degradation processes and for the endogenous consumption of glycogens, is carried out by a thermal treatment at a temperature comprised between 60° C. and 180° C. for a duration comprised between 30 seconds and 200 minutes or a chemical treatment with $Na_2CO_3$ or by means of an organic solvent, such as ethanol or propanol for example.

It can be provided, according to the invention, to carry out simultaneously or successively a thermal treatment and a chemical treatment of the yeast cells so as to obtain the mentioned deactivation.

The blockage of the metabolism of the yeast cells is preferably carried out when the latter have reached their maximum glycogen content in the course of the enrichment operation, the occurrence of value of this maximum content depending particularly on the nature of the age of said cells.

According to a first embodiment of the invention, the disintegration of the yeast cell walls can be carried out by mechanical milling by means of a high pressure homogenizer, a ball mill or a French press.

According to a second embodiment of the invention, the disintegration of the yeast cell walls can be carried out by means of non-mechanical treatments such as thermal treatments constituted by repeated cycles of freezing/thawing, enzymatic treatments using protease and hydrolase base preparations and chemical treatments by means of organic solvents, these treatments being adapted to be carried out singly or in combination.

According to a third embodiment of the invention, the disintegration of the yeast cell walls can be carried out by combining mechanical milling and at least one type of non-mechanical treatment.

The operation of disintegration of the yeast cells, which permits permeating or bursting the cell walls and freeing the intracellular substances, can be carried out with variable intensity as a function of the nature of the yeast and of the desired quality of the glycogen extract.

Thus, an increase of milling can permit extracting more glycogen, particularly that connected to the proteins of the cell wall, and lead to a greater solubilization of the other constituents of the cell walls.

So as to obtain a high quality final extract, the freed intracellular substances, after disintegration of the yeast cell walls, can be subjected to at least one treatment of fractionation, concentration and/or purification such as microfiltration, ultrafiltration or nanofiltration, electrodialysis, ion exchange adsorption or activated carbon adsorption and cryoconcentration.

The above treatments permit respectively fractionating, the constituents from milling the yeast cells, particularly the glucidic, proteic and nucleic macromolecules, concentrating the polysaccharides and the proteins, reducing the small molecule content (sugars, amino acids and peptides) and of soluble mineral elements, and decolorizing the solution resulting from milling.

According to another characteristic of the invention, the freed intracellular substances are preferably subjected to precipitation by acids such as hydrochloric or trichloroacetic acid, carried out at a pH comprised between 1 and 6 and at a temperature comprised between 0° C. and 60° C.

As a modification, the freed intracellular substances can be subjected to precipitation by salts such as ammonium sulfate, carried out at a pH comprised between 1 and 9, at a temperature comprised between 0° C. and 30° C. and with a salt content comprised between 100 and 80%.

According to still another modified embodiment of the invention, the freed intracellular substances can also be subjected to precipitation by alcohols, preferably ethanol or isopropanol, carried out at a pH comprised between 1 and 9, at a temperature comprised between 0° C. and 30° and with an alcohol content, by volume percent, comprised between 10% and 80%.

When the yeast cells treated by the present process are recovered as residues of a fermentation process, it can preferably be provided to subject the yeast cells, before the operation of enrichment in glycogens, to at least a washing with water at a temperature comprised between 10° C. and 60° C., if desired with the addition of a chemical agent such as $Na_2CO_3$, then to extract and concentrate said yeast cells, by centrifugation, decantation, filtration and/or microfiltration.

This operation or these operations of washing permit eliminating substances absorbed by the yeast cells or present in the suspension containing the latter.

Thus, in the case of yeast cells from brewery processes, this washing permits eliminating the hops extracts.

According to another characteristic of the invention, the freed intracellular substances can be subjected to at least one selective enzymatic hydrolysis treatment carried out by means of suitable preparations containing proteases, glucanases, mannases or a mixture of two or several of the mentioned enzymes.

These hydrolysis treatments permit reducing and even removing the content of certain glycidic and/or proteic macromolecules present in the yeast extracts.

Finally, the process according to the invention could also consist in concentrating, stabilizing and conditioning the obtained compositions by precipitation of the freed intracellular substances after disintegration of the yeast cells.

To this end, there can be carried out operations of evaporation or membrane filtration, the addition of adjuvants and/or drying and spraying or lyophilization operations.

According to the nature of the yeasts used and of the mentioned treatment processes that are used, the process for production and extraction according to the invention can gives glycogen compositions containing variable proportions of glycogens and of accompanying substances.

Thus, the extracts obtained by means of the process according to the invention can have a weight percent of glycogen, in dry condition, comprised between 5% and 99.9%, the extraction output being comprised as a function of the number and of the intensity of carrying out the operations involved, between 10% and 99%.

The mentioned accompanying substances can particularly comprise polysaccharides, in particular glucanes or mannanes, proteins, DNA and RNA molecules, hydrolysates of yeast polysaccharides, in particular of glycogens, of glucanes and of mannanes, hydrolysates of yeast proteins and saccharides such as trehalose.

The yeast glycogens or extracts of yeast rich in glycogens obtained by the invention can be used either in the raw form (aqueous solution) such as is obtained by the process according to the invention, or in various encapsulated or immobilized forms such as nanovesicles (liposomes . . . ), nanoparticles (nanospheres), microparticles (microspheres . . . ) or if desired in forms grafted with lipids, proteins or the like.

By way of non-limiting examples of practical embodiments of the invention, there will be described hereafter four examples of processes for the production and extraction of glycogens using the different operations and treatments mentioned above.

EXAMPLE 1

A process for the extraction of glycogens from Saccharomyces carlsbergensis cells at the end of brewery fermentation can for example comprise the following series of operations:

Thermal and chemical treatment of the yeast cells for 1 hour 30 minutes in $Na_2CO_3$ at 100° C.;

Crushing the cells by passage through a high pressure homogenizer (at 900 bars);

Centrifugation for 20 minutes at 4500 g;

Treatment of the supernatant with ethanol (2.4 l/l) at 40° C. to precipitate the glycogens or treatment of the supernatant from the grinding with isopropanol (2.4 l/l) at 4° C. to precipitate the glycogens;

Centrifugation and recovery of the precipitate.

This process permits obtaining a composition comprising particularly 25% of glycogens, 25% of proteins and 20% of residue.

EXAMPLE 2

A process for the production of glycogens with an initial enrichment of the yeast cells with glycogens and using a yeast from the end of brewery fermentation, can for example comprise the following series of operations:

Washing the yeast cells with water and centrifugation at 9500 rpm;

Culturing the yeast cells in a medium containing initially 10 g/l of glucose, 0.5 g/l of yeast extract, 3 g/l of $KH_2PO_4$, 0.9 g/l of $CaCl_2$ and 1 g/l of $MgSO_4$. Initially, the culture is formed in a discontinuous manner at 30° C. with a pH adjusted to 4.5 by the addition of 2N ammonia, and under aerobic conditions, with seeding with 50 g/l of yeast cells. Thereafter, the culture is continued with the addition of a solution of 500 g/l of glucose controlled to maintain the glucose level in the fermenter about 1 g/l (after 6 hours of culturing, obtaining 55 g/l by dry weight of yeast with 20% glycogens);

Recovery, washing and centrifugation of the yeast cells;

Extraction of the glycogens according to the process described in Example 1.

This process permits obtaining a composition containing particularly 38% of glycogens, 22% of proteins and 23% of residue.

EXAMPLE 3

A process for the production of glycogens from brewery yeast proceeding in an aerobic fermenter can for example comprise the following series of operations:

Production of Saccharomyces carlsbergensis yeasts by aerobic fermentation. Medium and culture conditions identical to those of Example 2, except for an initial seeding of yeast cells at 1 g/l (after 48 hours of culture, obtaining 50 g/l of yeast cells containing 21% glycogens);

Extraction of glycogens according to a process identical to that described in Example 1.

EXAMPLE 4

A process for the production of glycogens from yeast cells at the end of brewery fermentation, comprising a complementary purification treatment by acid precipitation, can for example be constituted by the following series of operations:

Thermal and chemical treatment of the yeast cells for 1 hour 30 minutes in $Na_2CO_3$ (0.25 M) at 100° C.;

Crushing of the cells by passage through a high pressure homogenizer (1 passage at 900 bars);

Centrifugation for 20 minutes at 4500 g;

Treatment of the supernatant with trichloroacetic acid (10% weight per volume), centrifugation and elimination of the precipitate;

Treatment of the supernatant with ethanol (2.4 l/l) at 4° C. to precipitate glycogens;

Centrifugation and recovery of the precipitate.

This process permits obtaining a compound comprising particularly 64% of glycogens and less than 1% of residue.

The present invention also has for its object the use of the glycogens or of an extract rich in glycogens obtained by the means of the process described above, as a constituent of a product, of a preparation or of a cosmetic composition, particularly adapted to be applied to the skin.

Such a cosmetic composition can preferably comprise glycogens or an extract rich in glycogens obtained as described above, the weight content of glycogens of said composition being comprised between 0.001% and 10%.

Preferably, the glycogens or extract rich in glycogens used, is obtained from yeast cells of the type selected from the group consisting of *Saccharomyces carlsbergensis, Saccharomyces uvarum, Saccharomyces cerevisiae, Zygosaccharomyces fermentati, Candida utilis, Candida tropicalis, Hansunela anomala, Kluyveromyces fragilis, Debaromyces marana, Dekkera naardenensis, Geotrichum penicillatum, Lipomyces starkeyi, Metschnikowia lunata, Paschysolen tannophilus, Pichia abadieae* and *Torulopsis ernobii*, preferably yeast cells from the end of brewery fermentation.

By way of non-limiting examples of practical embodiments of compositions according to the invention, there will be described hereafter different products or cosmetic preparations comprising glycogens obtained by means of the process according to the invention.

EXAMPLE 1

A cosmetic product in the form of a hand cream according to the invention could, for example, have a weight composition, constituted from fractions A, B and C as follows, as indicated hereafter.

| Fraction A: | |
| --- | --- |
| Cetostaryl alcohol (and) sodium cetostaryl sulfate | 7.00% |
| Stearic acid | 1.00% |
| Octyldodecanol | 3.00% |
| Fraction B: | |
| Distilled water | 48.40% |
| Preservative | 0.30% |
| Glycerine | 40.00% |
| Glycogens from yeast cells | 0.10% |
| Fraction C: | |
| Perfume | 0.20% |

The process of preparation and production of the hand cream above consists essentially in preparing a fatty phase A by heating it to 85° C., heating together the water and the glycerine at 75° C., dissolving the preservative, then adding the glycogens with agitation, continuing until complete dispersion-dissolution, pouring A into B with agitation (by means of a rotor), progressively cooling the A-B mixture, stopping at about 50° C. the agitation and proceeding only with planetary agitation and, finally, adding the fraction C (perfume) and continuing agitation, until complete cooling.

EXAMPLE 2

A cosmetic product in the form of a tonic lotion according to the invention could, for example, have a weight composition constituted by fractions A, B and C as indicated hereafter.

| Fraction A: | |
|---|---|
| Ethyl alcohol | 3.000% |
| Nonoxynol-14 | 0.600% |
| Perfume | 0.100% |
| Fraction B: | |
| Propylene glycol | 2.000% |
| Glycerine | 10.000% |
| Preservative | 0.300% |
| Distilled water | 73.735% |
| Triethanolamine | 0.060% |
| Fraction C: | |
| Distilled Witch Hazel | 9.500% |
| Sodium lactate | 0.700% |
| Glycogens from yeast cells | 0.005% |

The process of preparation and production of the tonic lotion above consists essentially in preparing fraction B, by heating at +45° C., with agitation until complete dissolution, preparing separately the solutions of fractions C and A by agitation at ambient temperature, mixing together the three solutions A, B and C, and, finally, filtering the obtained mixture.

EXAMPLE 3

A cosmetic product in the form of a sun protective cream according to the invention could, for example, have a weight composition constituted from the following fractions A and B, as indicated hereafter.

| Fraction A: | |
|---|---|
| Cetyl alcohol | 5.00% |
| Caprylic/capric triglycerine | 9.00% |
| Paraffin oil | 3.75% |
| Oil of lanoline | 1.00% |
| Glycerol stearate | 2.00% |
| Dimethicone | 0.25% |
| Octyldodecanol | 1.50% |
| Benzophenone-3 | 4.50% |
| Octyl methoxycinnamate | 7.50% |
| Fraction B: | |
| Distilled water | 54.10% |
| Preservative | 0.40% |
| Glycerine | 3.00% |
| Potassium cetyl phosphate | 3.00% |
| Glycogens of yeast cells | 5.00% |

The process of preparation and production of the sun protective cream above consists essentially in preparing fatty phase A by heating at 80° C., preparing aqueous phase B by heating at +75° C. with agitation, introducing phase A into phase B with agitation (at least by a rotor), continuing agitation and carrying out cooling to 65° C., stopping the rotor agitation at about 50° C. and maintaining only planetary agitation and, finally, continuing the agitation until the return of the mixture to room temperature.

Of course, the invention is not limited to the embodiment described. Modifications remain possible, particularly as to the construction of the various elements or by substitution of technical equivalents, without thereby departing from the scope of protection of the invention.

What is claimed is:

1. Process for the production of glycogens from viable yeast cells, comprising subjecting said viable yeast cells to an operation of enrichment in intracellular glycogens comprising in a first phase culturing the viable yeast cells in a nutrient medium comprising a source of carbon, nitrogen, phosphorus, mineral elements and vitamins, and in a second maturation phase continuing culturing of said yeast cells in a nutrient medium containing at least one carbon source at a concentration comprised between 1 and 700 g per liter of nutrient medium, and a source of nitrogen such that the viable yeast cells transform the carbon source into intracellular glycogens, stopping metabolism of said viable yeast cells, disintegrating at least partially the membranes of said viable yeast cells to free soluble intracellular substances, and subjecting the freed soluble intracellular substances to at least one precipitation to precipitate glycogens and recovering said glycogens.

2. Process according to claim 1, wherein the stopping of the metabolism of the yeast cells is obtained by carrying out a thermal treatment at a temperature comprised between 60° C. and 180° C. for a duration comprised between 30 seconds and 200 minutes or a chemical treatment with $Na_2Co_3$ or an organic solvent.

3. Process according to claim 2, wherein said stopping of the metabolism of the yeast cells is obtained by simultaneously or successively treating the yeast cells with thermal treatment and chemical treatment means.

4. Process according to claim 1, wherein the disintegration of the yeast cell walls is carried out by mechanical crushing means comprising a high pressure homogenizer, a ball mill or a French press.

5. Process according to claim 4, wherein the disintegration of the yeast cell membranes is carried out by combining mechanical crushing and at least one type of non-mechanical treatment.

6. Process according to claim 1, wherein the disintegration of the yeast cell walls is carried out by non-mechanical treatments comprising thermal treatment constituted by repeated cycles of freezing/thawing, enzymatic treatments using protease and hydrolase base preparations or chemical treatments with organic solvents, used alone or in combination.

7. Process according to claim 1, wherein the intracellular substances freed after disintegration of the yeast cell membranes are subjected to at least one treatment prior to said precipation selected from the group consisting of fractionation, concentration and/or purification comprising microfiltration, ultrafiltration or nanofiltration, electrodialysis, ion exchange adsorption, adsorption by active carbon and cryoconcentration.

8. Process according to claim 1, wherein the freed intracellular substances are subjected to said precipitation by acids, carried out at a pH between 1 and 6 and at a temperature between 0° C. and 60° C.

9. Process according to claim 1, wherein the freed intracellular substances are subjected to said precipitation by salts, carried out at a pH between 1 and 9, at a temperature between 0° C. and 30° C. and with a salt content between 10% and 80%.

10. Process according to claim 1, wherein the freed intracellular substances are subjected to said precipitation by alcohols, carried out at a pH between 1 and 9, at a temperature between 0° C. and 30° C. and with an alcohol content by volume ratio between 10% and 80%.

11. Process according to claim 1, which further comprises, before the operation of enrichment in glycogens, subjecting the yeast cells to at least one washing with water at a temperature between 10° C. and 60° C., then extracting and concentrating said yeast cells, by centrifugation, decantation, filtration and/or microfiltration.

12. Process according to claim 1, wherein the freed intracellular substances are subjected to at least one selective enzymatic hydrolysis treatment prior to precipation with a preparation containing proteases, glucanases, mannases or mixtures thereof.

13. Process according to claim 1, which further comprises concentrating, stabilizing and conditioning glycogens obtained by said precipitation.

14. A cosmetic composition comprising glycogens prepared by the process of claim 1, in admixture with a dermatologically acceptable excipient.

15. A cosmetic composition as claimed in claim 14, containing between 0.001% and 10% by weight of said glycogens.

16. A cosmetic composition according to claim 14, wherein said glycogens are obtained from yeast cells selected from the group consisting of *Saccharomyces carlsbergensis, Saccharomyces uvarum, Saccharomyces cerevisiae, Zygosaccharomyces fermentati, Candida utilis, Candida tropicalis, Hansunela anomala, Kluyveromyces fragilis, Debaromyces marana, Dekkera naardenensis, Geotrichum penicillatum, Lipomyces starkeyi, Metschnikowia lunata, Paschysolen tannophilus, Pichia abadieae* and *Torulopsis ernobii*.

* * * * *